United States Patent
He

(10) Patent No.: US 11,849,770 B2
(45) Date of Patent: Dec. 26, 2023

(54) METHOD FOR DETECTING THE NUMBER OF PUFFS OF AN ELECTRONIC CIGARETTE, AND ELECTRONIC CIGARETTE

(71) Applicant: DONGGUAN MYSMOK ELECTRONIC TECHNOLOGY CO., LTD, Guangdong (CN)

(72) Inventor: Liqing He, Guangdong (CN)

(73) Assignee: DONGGUAN MYSMOK ELECTRONIC TECHNOLOGY CO., LTD, Dongguan (CN)

(*) Notice: Subject to any disclaimer, the term of this patent is extended or adjusted under 35 U.S.C. 154(b) by 756 days.

(21) Appl. No.: 17/060,224

(22) Filed: Oct. 1, 2020

(65) Prior Publication Data

US 2021/0015165 A1 Jan. 21, 2021

Related U.S. Application Data

(63) Continuation-in-part of application No. PCT/CN2019/086103, filed on May 9, 2019.

(51) Int. Cl.
*A24F 40/53* (2020.01)
*A24F 40/57* (2020.01)
(Continued)

(52) U.S. Cl.
CPC .............. *A24F 40/53* (2020.01); *A24F 40/51* (2020.01); *A24F 40/57* (2020.01); *A24F 40/60* (2020.01); *G06F 17/11* (2013.01)

(58) Field of Classification Search
CPC .......... A24F 40/51; A24F 40/53; A24F 40/57; A24F 40/60; G06F 17/11
See application file for complete search history.

(56) References Cited

U.S. PATENT DOCUMENTS

8,499,766 B1 * 8/2013 Newton .................. A24F 40/51
131/273
9,961,941 B2 * 5/2018 Tucker ..................... A24F 40/48
(Continued)

FOREIGN PATENT DOCUMENTS

CN 107951078 A 4/2018
CN 108459536 A 8/2018
(Continued)

*Primary Examiner* — Thanh Tam T Le
(74) *Attorney, Agent, or Firm* — SHIMOKAJI IP

(57) ABSTRACT

A method for detecting the number of puffs of an electronic cigarette, includes sampling a real-time temperature of a heating unit, and determining a temperature difference; integrating the temperature difference in time to obtain an integral value I; calculating a first limit H according to the integral value I; and judging whether the real-time integral value I is beyond the first limit value H, if yes, determining that one puff of smoking happens. The method calculates a limit value that is a real-time value and varied with the change trend and change amplitude of the temperature difference. When the environment or the usage habit changes, the corresponding first limit can still be calculated according to the integral value of the current temperature difference to accurately determine the smoking behavior, thereby effectively improving the detection accuracy of the number of puffs of smoking.

19 Claims, 5 Drawing Sheets

(51) Int. Cl.
    *A24F 40/51*     (2020.01)
    *A24F 40/60*     (2020.01)
    *G06F 17/11*     (2006.01)

(56) References Cited

U.S. PATENT DOCUMENTS

| | | | | |
|---|---|---|---|---|
| 10,206,433 | B2* | 2/2019 | Ding | H05B 1/0227 |
| 10,412,997 | B2* | 9/2019 | Cameron | H04W 4/12 |
| 10,721,963 | B2* | 7/2020 | Thorens | A61M 11/042 |
| 11,399,573 | B2* | 8/2022 | Aradachi | H02J 7/0042 |
| 11,589,621 | B2* | 2/2023 | Sur | A24F 40/65 |
| 11,606,978 | B2* | 3/2023 | Cornils | A61M 15/06 |
| 11,611,227 | B2* | 3/2023 | Yamada | A61M 15/009 |
| 11,641,885 | B2* | 5/2023 | Garris | A24F 40/53 |
| | | | | 73/865.8 |
| 11,696,602 | B2* | 7/2023 | Flora | A24F 40/53 |
| | | | | 131/329 |
| 11,698,717 | B2* | 7/2023 | Amorde | A61M 16/18 |
| | | | | 128/202.21 |
| 11,744,285 | B2* | 9/2023 | Lacovara | A24F 40/53 |
| | | | | 131/329 |

FOREIGN PATENT DOCUMENTS

| | | |
|---|---|---|
| CN | 108572202 A | 9/2018 |
| CN | 108873981 A | 11/2018 |
| CN | 108991605 A | 12/2018 |
| KR | 20190010432 A | 1/2019 |

\* cited by examiner

METHOD FOR DETECTING THE NUMBER OF PUFFS OF AN ELECTRONIC CIGARETTE, AND ELECTRONIC CIGARETTE

FIELD OF THE INVENTION

The present invention relates to the technical field of electronic cigarettes, and more particularly to a method for detecting the number of puffs of a heated electronic cigarette and an electronic cigarette.

BACKGROUND OF THE INVENTION

There are many carcinogens in the smoke of tobacco burning, such as tar, which will cause harm to human health for long-term inhalation. Moreover, tobacco smoke in the air will form second-hand smoke, which may also bring health risks for the surrounding people. Therefore, smoking is explicitly prohibited in most public places. In order to meet the needs of smokers, electronic cigarettes came into being.

In the prior art, one method for the electronic cigarette device to determine the number of puffs of smoking is realized by an air switch provided on the electronic cigarette device. Specifically, the air switch is configured to record the airflow when the user smokes, and the number of puffs to smoke is determined according to the airflow.

However, the method of determining the number of puffs of smoking through the air switch or an air pressure sensor requires the setting of a special air switch or air pressure sensor to record the data detected by the airflow, which makes the cost of the electronic cigarette relatively high.

In addition, another method of determining the number of puffs of smoking is based on simple temperature fluctuations. However, temperature fluctuation occurs easily, because the heat capacity of the heating object of the tobacco type electronic cigarette is small. For example, when using an electronic cigarette, the electronic cigarette is held by the user and may be shaken frequently, thus air flow inside the electronic cigarette will happen to take away some of the heat, resulting in a temperature decrease. In this case, the number of puffs of smoking calculated based on simple temperature fluctuation is often inaccurate. For example, the number of puffs of smoking is misjudged, if one puff of smoking is determined when temperature is reduced to a threshold temperature; the misjudgment will be decreased if the threshold temperature is set higher, nevertheless, a puff of smoking w ill not be recorded when the smoker smokes lightly and that threshold temperature does not reach. Therefore, it is difficult for tobacco type electronic cigarette to overcome the problems of omission and misjudgment in calculating the number of puffs of smoking.

For example, the Chinese invention patent application with application publication number CN108991605A discloses a method for judging the number of puffs of smoking of an electronic cigarette and an electronic cigarette. The method includes the following steps: setting the target temperature of the heating element of the electronic cigarette; detecting and acquiring the current temperature of the heating element; determining a temperature difference according to the target temperature and the current temperature; repeating to collect the temperature difference if the temperature difference is less than a starling threshold; integrating the temperature difference in time if the temperature difference is larger than the starting threshold, stopping the integration once the temperature difference is less than the starting threshold, and determining a current integral value; and determining one puff of smoking if the current the temperature difference is larger than an judgment threshold. In such a way, the accuracy rate of judging the number of puffs of smoking is improved, to a certain degree. However, this judgment method still has accuracy and problems. For example, the temperature difference integral value of the heating element fluctuates due to certain reasons, which may still be misjudged as one puff of smoking. On the other hand, the starting threshold in this detection method is a fixed value, which remains unchanged although the environment changes or the user's frequency of use changes, thereby leading a judgment result. Furthermore, since the detection method counts a puff of smoking when the integral value is larger than the judgment threshold, thus one puff of smoking is still misjudged when the integral value jumps due to system instability and other reasons.

Therefore, the existing method for detecting the number of puffs of an electronic cigarette still needs to be improved and developed to make the detection more reliable, stable and accurate.

SUMMARY OF THE INVENTION

The technical problem to be solved by the present invention is to provide a method for detecting the number of puffs of an electronic cigarette and an electronic cigarette, which aims at overcoming the above-mentioned shortcomings of the prior art, and obtaining high detection accuracy.

To achieve the mentioned above objective, the present invention provides a method for detecting the number of puffs of an electronic cigarette, including: step (1), sampling to obtain a real-time temperature of a heating unit of the electronic cigarette, and determining a temperature difference between a target temperature and the real-time temperature; step (2), integrating the temperature difference in time to obtain an integral value I that is real-time; step (3), calculating a first limit H that is real-time according to the integral value I; and step (4), judging whether the real-time integral value I is beyond the first limit value H, if yes, determining that one puff of smoking happens.

In comparison with the prior art, the present invention calculates a limit value in real time based on the integral of the temperature difference between the real-time temperature and the target temperature in time as a comparison threshold value (the first limit H) for judging smoking behavior. The limit value is not a rated fixed value, but a real-time value that is varied with the change trend and change amplitude of the temperature difference. When the environment or the usage habit changes, the corresponding first limit can still be calculated according to the integral value of the current temperature difference to accurately determine the smoking behavior, thereby effectively improving the detection accuracy of the number of puffs of smoking.

Preferably, the step (3) includes integrating the integral value I in time to obtain the first limit value H. In such a way, the current integral value I is integrated in time to determine the real-time first limit value II, and the calculation is convenient and accurate. Of course, other methods can also be used to calculate the real-time first limit H, such as using the integral value I to calculate the average value over a period of time to adjust the current first limit H Preferably, the step (3) includes integrating the integral value I in a current time period to obtain the first limit value H. The current time period is the time domain within a period of time that is at the front of the current time, or a period to time related to the current time.

Specifically, in the step (3), the first limit H is calculated by using a formula $H \times K_h \int_{t2}^{t1} Idt/c$, wherein t1 represents a current time, t2 represents t1−Δt, Δt represents a preset time domain, C represents sampling times within Δt seconds, C=Δt/Δt', Δt' represents a sampling interval within Δt seconds, and $K_h$ represents a preset constant. By introducing the sampling times C, the calculation accuracy is improved.

More specifically, a value condition of $K_h$ is limited as following: the first limit value H is greater than the integral value I when no smoking behavior happens, and the first limit value H is smaller than the integral value I when smoking behavior happens. $K_h$ can be determined by testing and empirical heating parameters of the electronic cigarette.

Preferably, the step (4) specifically includes judging whether the integral value I keeps to be beyond the first limit value H for a preset time T3, if yes, determining that one puff of smoking happens. That is to say, the puff of smoking will not be determined until the integral value is beyond the first limit value H for a preset time.

Preferably, the step (4) further includes recording one puff when said puff of smoking is determined. In such a way, the current total number of puffs of smoking can be obtained in real time, which is convenient for corresponding operations, such as instruction, shutdown, etc., based on the total number of puffs of smoking.

Preferably, the method further includes a step (5): judging whether the real-time temperature is under a stable condition, if yes, detecting a next puff of smoking. By this token, the detection is started up under a stable condition, so as to improve the detection accuracy.

Specifically, the step (5) specifically includes judging whether the integral value I is beyond the first limit value H, if yes, determining that the real-time temperature is under a stable condition.

More preferably, the step (5) further specifically includes judging whether the integral value I is between the first limit value H and a second limit value L, if yes, determining that the real-time temperature is under a stable condition. That is to say, the detection will not be performed until the real-time temperature is under a stable condition.

Specifically, the second limit value L is a preset value or a real-time value calculated according to the integral value I, thereby improving the accuracy of the judgment result.

More preferably, the second limit value L that is real-time is obtained by integrating the integral value I in the current time period, thereby further improving the detection accuracy.

Specifically, the second limit value L is calculated by using a formula $L = K_l \int_{t2}^{t1} 1Idt/c$, wherein t1 represents a current time, t2 represents t1−Δt, Δt represents a preset time domain, C represents sampling times within Δt seconds, C=Δt/Δt', Δt' represents a sampling interval within Δt seconds, and $K_h$ represents a preset constant. By introducing the sampling times C, the calculation accuracy is improved.

Preferably, the method further includes establishing a variation curve model of integral value of the temperature difference of heating unit on a time axis, based on the integrated value I, the first limit value H, and the second limit value L; wherein the variation curve model includes a curve of integrated value I curve, a curve of first limit H and a curve of second limit L, varying along the time axis. Therefore, it's convenient for monitoring.

Preferably, in the step (2), the temperature difference is integrated in real time so as to obtain the integral value I that is real-time. Compared with the prior art, the temperature difference is not judged by the threshold value, but the real-time calculated temperature difference is integrated in real time to obtain the integral value I, which reduces the misjudgment of the number of puffs of smoking due to environmental fluctuations and user actions.

Preferably, before the step (1), the method further includes a step of performing constant temperature control: setting a target temperature of the heating unit, preheating the heating unit, and performing constant temperature control on the heating unit based on PID. In such a way, this solution makes it possible to perform compensation control when smoking and other actions cause the real-time temperature to deviate from the target temperature, so that the real-time temperature will deviate from the target temperature in a later period of time. Not only the temperature control speed is fast, but also the real-time integral value I can always locate in a relatively balanced fluctuation range, so that the present invention can perform detection based on steady temperature changes.

The present invention further provides an electronic cigarette including a heating unit, one or more processors, a memory, and one or more programs stored in the memory, wherein the one or more programs are configured to be driven by said one or more processors and configured to execute the method. Compared with the prior art, the present invention can accurately detect the number of smoking puffs and reduce misjudgments.

Preferably, the electronic cigarette further includes a prompt module, and the one or more processors is further configured to control the prompt module to prompt the number of puffs of smoking.

Specifically, the prompt module is configured to prompt the number of puffs of smoking by voice prompt, display screen prompts, or on/off lights indication.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The present invention will be described in detail below with reference to the accompanying drawings and preferred embodiments.

Figure 1:
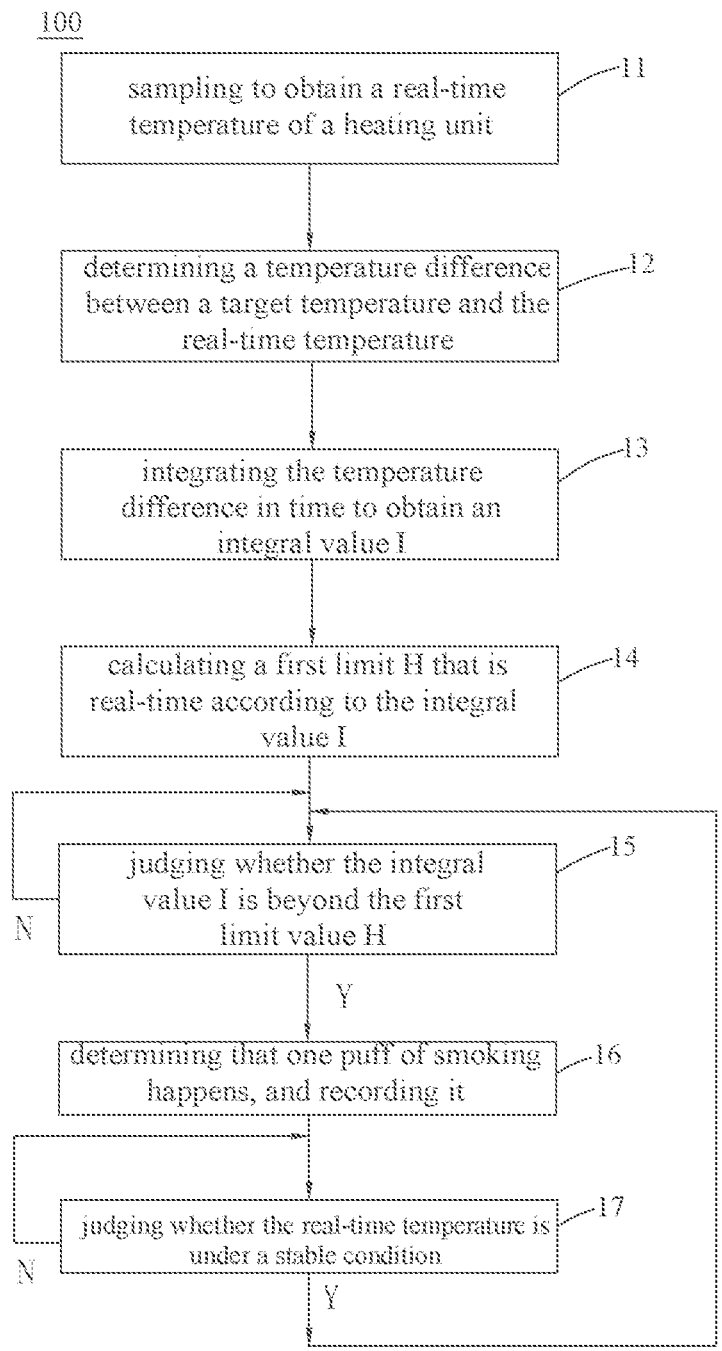
FIG. 1 is a flowchart of a method for detecting the number of puffs of an electronic cigarette according to a first embodiment of the present invention.

As illustrated in FIG. 1, a method 100 for detecting the number of puffs of an electronic cigarette includes following steps of: 11, sampling to obtain a real-time temperature of a heating unit of the electronic cigarette; 12, determining a temperature difference between a target temperature and the real-time temperature; 13, integrating the temperature difference in time to obtain an integral value I that is real-time; 14, calculating a first limit H that is real-time according to the integral value I; 15, judging whether the integral value I is beyond the first limit value H, if yes. 16, determining that one puff of smoking (smoking behavior) happens, if not, returning to the step 15.

Specifically, in the step 16, when one puff of smoking happens, once puff will be recorded, in such a way, the total pull's may be determined.

In the present embodiment, in the step 13, the real-time integral value I is obtained by integrating the temperature difference in time, without using a temperature threshold. In such a way; not only the judgment result is accurate, but also it is convenient to obtain the first limit value H in step 14.

Preferably, the step 14 specifically includes integrating tire real-time integral value I in time to obtain the real-time first limit value H. Specifically, in step 14, the real-time first limit value H is obtained by integrating the integral value I in a current time period. More specifically, the current time period is the time domain within a period of time that is at the front of the current time, for example, the current time is t1, and the current time period is the time period from t1 to t1−Δt, and Δt represents a preset time domain. Of course, in another embodiment, the current time period may also be a time period from t1−Δt1 to t1−Δt2, wherein Δt1 and Δt2 represent preset time domains, and Δt1 is greater than Δt2. Of course, in another embodiment, the current time period can also be a period that is at the front of the current time, that is between ti to ti−Δt3, wherein Δt3 represents a preset time domain. That is, the current time period is a time period corresponding to the current time t1.

More specifically, the first limit value H is calculated by using the formula H=$K_h \int_{t2}^{t1} 1 I dt/c$, where t1 represents the current time, t2 represents t1−Δt, Δt represents the preset time domain, C represents the sampling times in Δt seconds, C=Δt/Δt', Δt represents the sampling interval in Δt seconds, $K_h$ represents the preset constant, in this embodiment, the sampling frequency C is introduced to improve calculation accuracy and detection accuracy. Of course, the current time t1 can be replaced by a time point corresponding to t1, such as t1−Δt1 and t1 mentioned above.

Specifically, the value condition of $K_h$ is limited as following: the first limit value H is greater titan the integral value I when not smoking, and the first limit value H is smaller than the integral value I when smoking. $K_h$ can be determined by testing and empirical hearing parameters of the electronic cigarette.

Preferably, the method 100 of further includes step 17: judging whether the real-time temperature is under a stable condition, if yes, detecting a next puff of smoking (step 15). Specifically, the steps 11-14 are real-time calculations, and the step 17 is performed after the step (16).

Preferably, the step 17 includes judging whether the real-time integral value I is beyond the first limit value H, if yes, determining the real-time temperature to be under a stable condition. Preferably, the step 17 includes judging whether the integral value I is beyond the first limit value H for a preset time period T4, if yes, the real-time temperature is under a stable condition.

In this embodiment, temperature difference=target temperature−real-time temperature. In the step 15, if the real-time integral value I is larger than the real-time first limit value H, it's determined that, the real-time integral value I is beyond the integral value I, in the step 17, if the real-time integral value I is smaller than the real-time first limit value H, it's determined that, the real-time integral value I is beyond the real-time integral value I.

Figure 2:
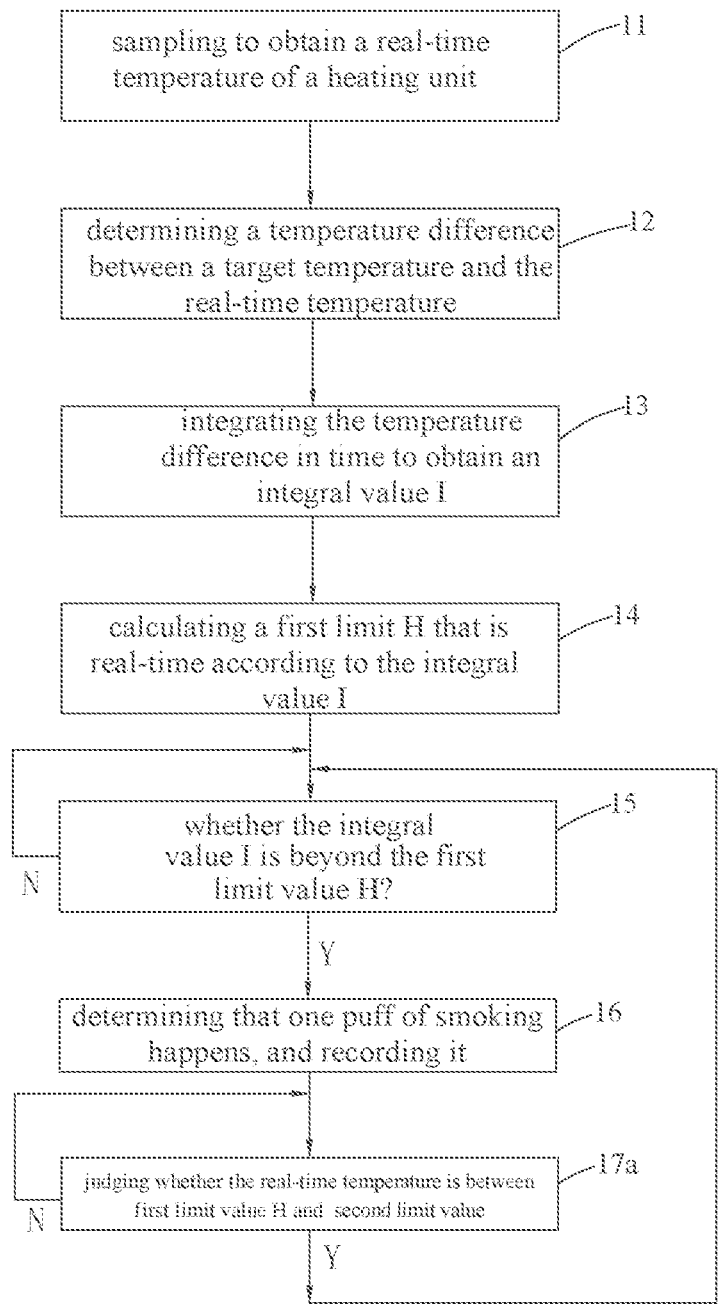
FIG. 2 is a flowchart of a method for detecting the number of puffs of an electronic cigarette according to a second embodiment of the present invention.

Referring to FIG. 2, differing from the first embodiment, in the second embodiment of the present invention, the step 17a of how to judge the real-time temperature to be under a stable condition specifically includes: judging whether the real-time integral value I is between the first limit value H and a second limit value L, if yes, determining that the real-time temperature is under a stable condition (step 15). Alternatively, the step 17a can also be replaced by: determining whether the integral value I is maintained to be between the first limit value H and the second limit value L for a preset time T4, if yes, determining that the real-time temperature is in a stable condition (as shown in step 17b in FIG. 2).

Specifically, temperature difference=target temperature−real-time temperature. In the step 15, if the real-time integral value I is larger than the real-time first limit value H, it's determined that, the real-time integral value I is beyond the real-time integral value I, in the step 17a, if the real-time integral value I is smaller than the first limit value H and larger than the second limit value L, it's determined that, the real-time integral value I is between the first limit value H and the second limit value L.

Specifically, the second limit value L is a preset value or a real-time value calculated according to the integral value I. In this embodiment, the second limit value L is a real-time value. Specifically, before the step 17, the method further includes integrating the integral value I in the current time period to obtain the real-time second limit value L, in such a way, the detection accuracy is improved.

Specifically, the real-time second limit value L is calculated by the following formula L=$K_l \int_{t2}^{t1} 1 I dt/c$, wherein t1 represents a current time, t2 represents t1−Δt, Δt represents a preset time domain, and C represents sampling times within Δt seconds, C Δt/Δt', Δt' represents a sampling interval within Δt seconds, represents a preset constant. By intruding the sampling times C, the accuracy of calculation is improved.

Figure 3:
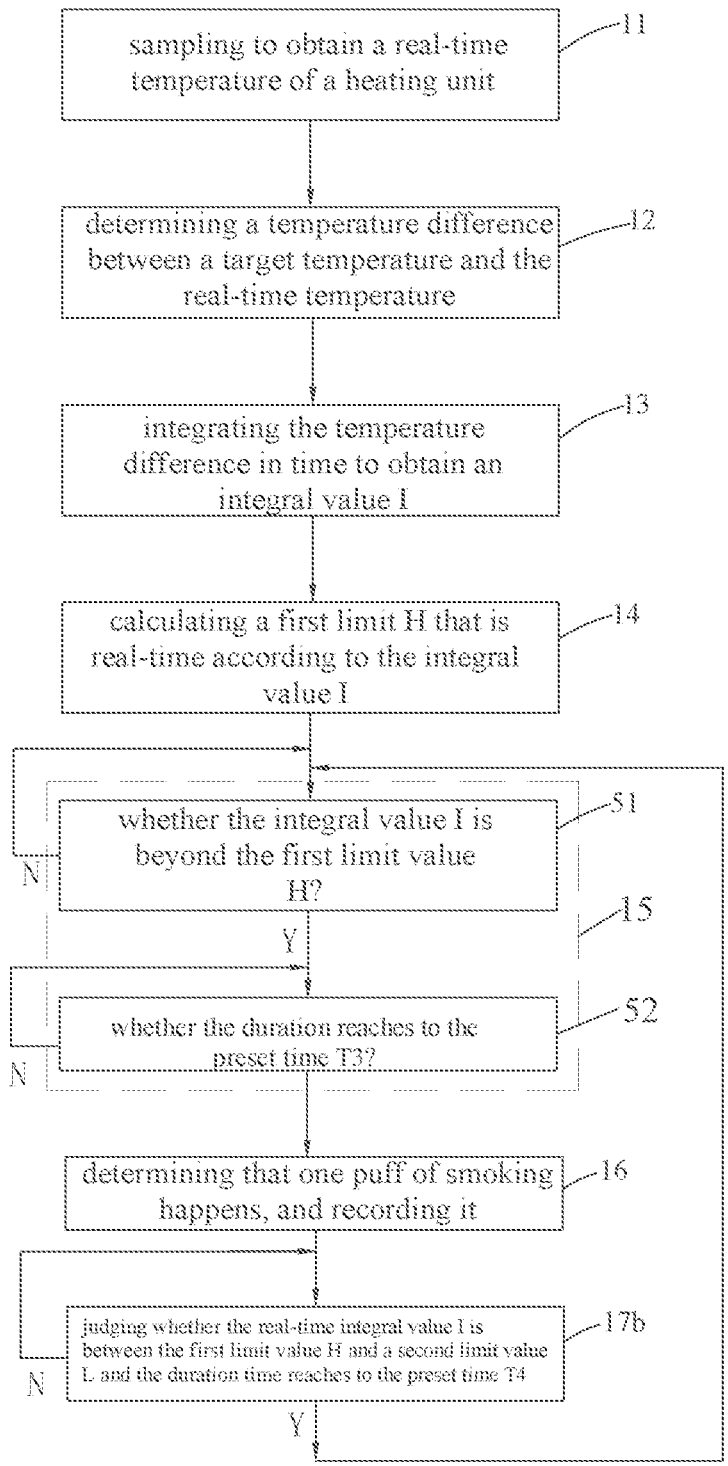
FIG. 3 is a flowchart of a method for detecting the number of puffs of an electronic cigarette according to a third embodiment of the present invention.

Referring to FIG. 3, differing from the second embodiment, in the third embodiment of the present invention, the step 15 specifically includes judging whether the real-time integral value I keeps to be beyond the real-time first limit value H for a preset time T3, if yes, determining that one puff of smoking happens.

Specifically, the step 15 includes judging whether the real-time integral value I is beyond the real-time first limit value H, if yes, performing the step 52 of timekeeping and judging whether the duration reaches to the preset time T3, if yes, performing the step 16 of determining that one puff of smoking happens.

More specifically, a timer is set. In the step 52, the timer is started to count, and it is judged whether the duration time is greater than the preset time T3, if yes, one puff of smoking is determined (step 16). Specifically, in the timing process, if the real-time integral value f does not exceed the real-time first limit value H, the timer stops and clears. Before restarting the detection of the number of puffs, the timer is cleared. Of course, it is not limited to the above-mentioned embodiment.

In the present embodiment, the step 17b includes judging whether the real-time integral value I is between the first limit value H and a second limit value L and the duration time reaches to the preset time T4, if yes, determining that the real-time temperature is under a stable condition.

Figure 4:
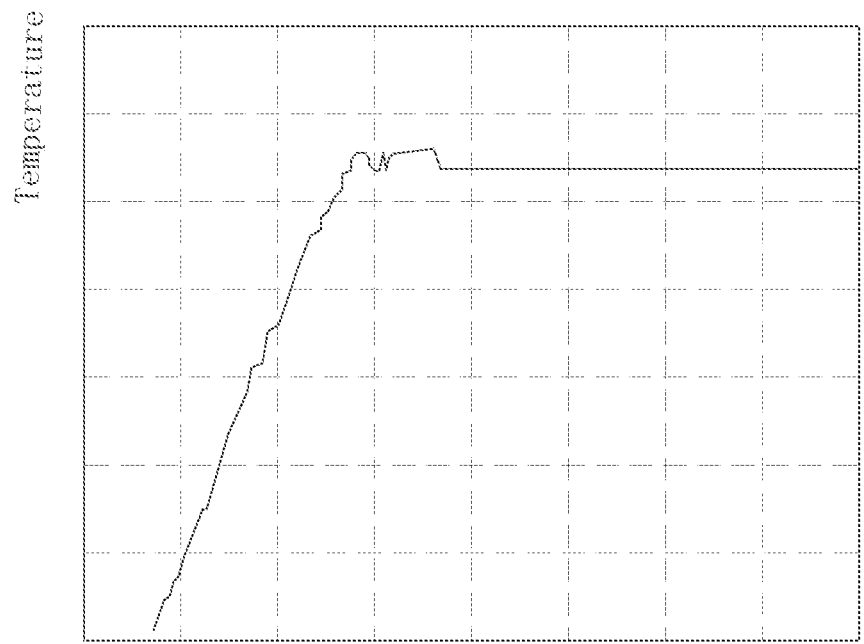
FIG. 4 is a schematic diagram of the temperature change of the heating unit.

Based on the above embodiment, before the step 11, the method further includes a step of performing constant temperature control: setting a target temperature of the heating unit, and performing constant temperature control on the heating unit based on PID control after preheating. Referring to FIG. 4 showing the temperature change of the heating unit 21, the temperature changes from the climbing during the preheating to the final stabilization.

In the present embodiment, under the constant temperature control condition of the PID control unit, the real-time temperature difference integral value I and the first limit value H and the second limit value L are calculated, and a limitation of the duration time is executed, which accurately determines a smoking behavior so as to effectively avoid miscalculation, and dynamically knows the real-time temperature status, thereby being in line with the actual temperature change status to achieve more accurate detection.

Figure 5:
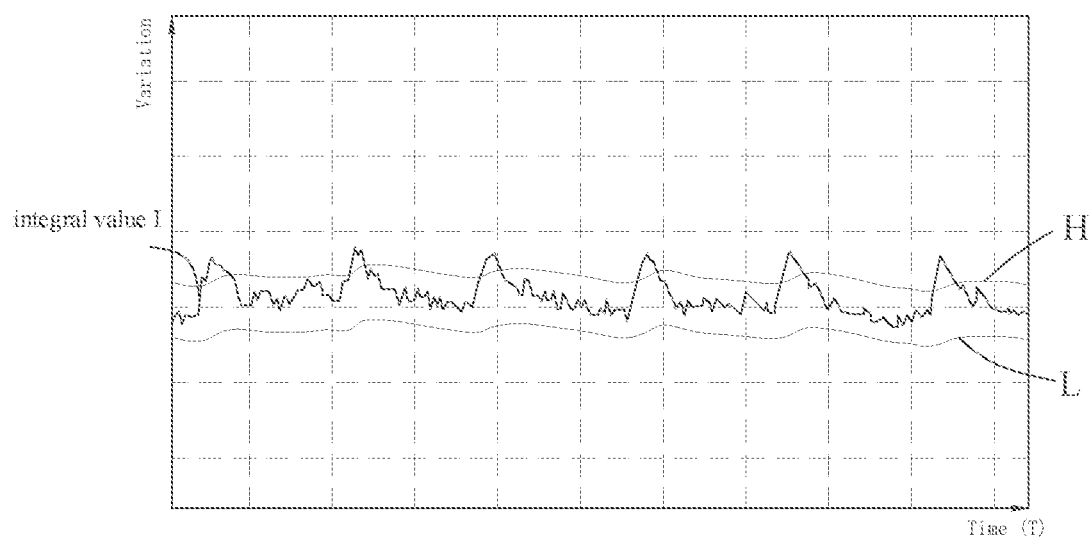
FIG. 5 is a schematic diagram of curves of integral value I, first limit value H, and second limit value L of the present invention in time axis and variation axis.

FIG. 5 is a variation curve model of integral value of the temperature difference of heating unit on a time axis, based on the integrated value f, the first limit value I, and the second limit value L. The curve model includes a curve of integral value I, a curve of first limit H, a curve of second limit L, changing on the time axis, for monitoring.

Figure 6:
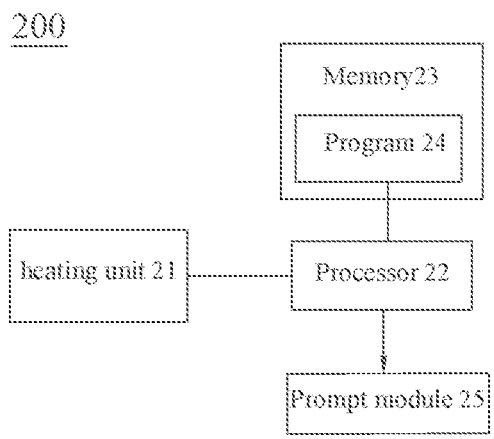
FIG. 6 is a structural block diagram of an electronic cigarette according to one embodiment of the present invention.

Referring to FIG. 6, the present invention also discloses an electronic cigarette 200 including a heating unit 21, one or more processors 22, a memory 23 and one or more programs 24, wherein the one or more programs 24 are stored in the memory 23, the program 24 is configured to be driven by the processor 22 and configured to execute the method 100 for detecting the number of puff's of an electronic cigarette as described above.

Continuing to refer to FIG. 6, the electronic cigarette 200 further includes a prompt module 25, and the processor 22 is further configured to control the prompt module 25 to remind the number of puffs of smoking. Specifically, the prompt module 25 is configured to prompt the number of puffs of smoking by voice prompt, display screen prompt, or on/off lights indication. More specifically, voice prompt can report the number of puffs of smoking or the number of remaining puffs; display screen can show the number of puffs of smoking or the number of remaining putts; and the on/off lights can indicate the status of the smoking. For example, a row of LED lights is set, all LED lights are turned on if no smoking behavior happens, and one of the LED lights will be turned off when one puff of smoking happens. Of course, the above prompting ways can be individual or combined, which can be increased or decreased according to design requirements.

Figure 7:
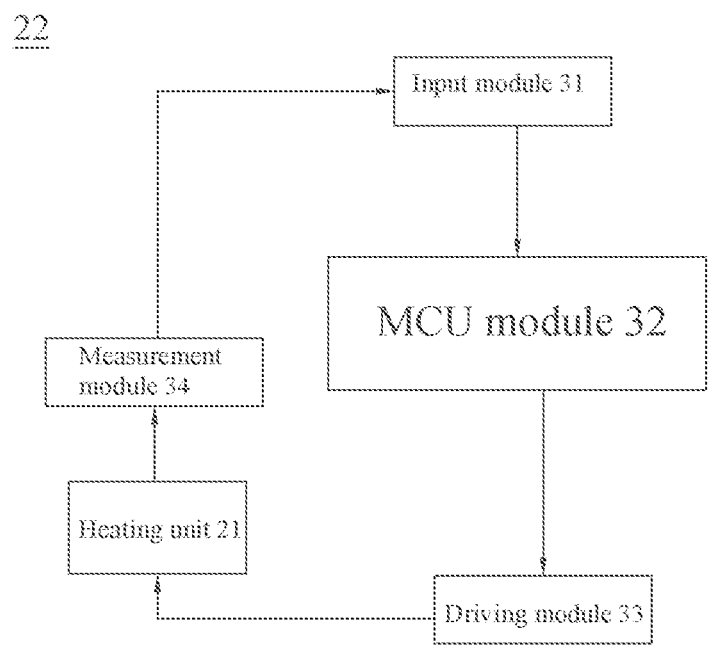
FIG. 7 is a structural block diagram of a processor of an electronic cigarette according to one embodiment of the present invention.

Referring to FIG. 7, the processor 22 includes an input module 31, an MCU module 32, a driving module 33, and a measurement module 34. The measurement module 34 is configured to detect the temperature of the heating unit 21 and transmit the detected temperature data to the input module 31. The input module 31 is connected to the MCU module 32 and configured to input the temperature data detected by the measurement module 34 to the MCU module 32. The MCU module 32 is configured to perform calculation processing such as proportional adjustment, integral adjustment, and differential adjustment on the temperature data so as to generate corresponding constant temperature control signal which is sent to the driving module 33. The driving module 33 is configured to control the action of the heating unit 21 according to the constant temperature control signal so that the heating unit 21 realizes constant temperature heating, as shown in FIG. 4 for details. In this embodiment, the MCU module 32 is further configured to drive the program 24 to execute the method 100 for detecting the number of puffs of the electronic cigarette. Additionally, the specific process of controlling the constant temperature of the heating unit 21 is well known to those of ordinary skill in the art, and thus no detailed description will be given here.

The foregoing description of the present invention has been presented for purposes of illustration and description, it is not intended to be exhaustive or to limit the invention to the precise form disclosed, and obviously many modifications and variations are possible in light of the above teaching. Such modifications and variations that may be apparent to those skilled in the art are intended to be included within the scope of this invention as defined by the accompanying claims.

What is claimed is:

1. A method for detecting the number of puffs of an electronic cigarette, comprising:
    step (1), sampling to obtain a real-time temperature of a heating unit of the electronic cigarette, and determining a temperature difference between a target temperature and the real-time temperature;
    step (2), integrating the temperature difference in time to obtain an integral value I that is real-time;
    step (3), calculating a first limit H that is real-time according to the integral value I; and
    step (4), judging whether the real-time integral value I is beyond the first limit value H, if yes, determining that one puff of smoking happens.

2. The method according to claim 1, wherein the step (3) comprises integrating the integral value I in time to obtain the first limit value H.

3. The method according to claim 2, wherein the step (3) comprises integrating the integral value I in a current time period to obtain the first limit value H.

4. The method according to claim 3, wherein in the step (3), the first limit H is calculated by using a formula $H=K_h \int_{t2}^{t1} I dt/c$, wherein t1 represents a current time, t2 represents t1−Δt, Δt represents a preset time domain, C represents sampling times within Δt seconds, C=Δt/Δt', Δt' represents a sampling interval within Δt seconds, and $K_h$ represents a preset constant.

5. The method according to claim 4, wherein a value condition of $K_h$ is limited as following: the first limit value H is greater than the integral value I when no smoking behavior happens, and the first limit value H is smaller than the integral value I when smoking behavior happens.

6. The method according to claim 1, wherein the step (4) specifically comprises: judging whether the integral value I keeps to be beyond the first limit value H for a preset time T3, if yes, determining that one puff of smoking happens.

7. The method according to claim 1, wherein the step (4) further comprises recording one puff when said puff of smoking is determined.

8. The method according to claim 1, further comprising step (5): judging whether the real-time temperature is under a stable condition, if yes, detecting a next puff of smoking.

9. The method according to claim 8, wherein the step (5) specifically comprises: judging whether the integral value I is beyond the first limit value H, if yes, determining that the real-time temperature is under a stable condition.

10. The method according to claim 9, wherein the step (5) further specifically comprises: judging whether the integral value I is between the first limit value H and a second limit value L, if yes, determining that the real-time temperature is under a stable condition.

11. The method according to claim 10, wherein the second limit value L is a preset value or a real-time value calculated according to the integral value I.

12. The method according to claim 11, wherein the second limit value L that is real-time is obtained by integrating the integral value I in the current time period.

13. The method according to claim 12, wherein the second limit value L is calculated by using a formula $L=K_h\int_{t2}^{t1} I dt/c$, wherein t1 represents a current time, t2 represents t1−Δt, Δt represents a preset time domain, C represents sampling times within Δt seconds, C=Δt/Δt', Δt' represents a sampling interval within Δt seconds, and $K_h$ represents a preset constant.

14. The method according to claim 9, further comprising establishing a variation curve model of integral value of the temperature difference of heating unit on a time axis, based on the integrated value I, the first limit value H, and the second limit value L; wherein the variation curve model includes a curve of integrated value I curve, a curve of first limit H and a curve of second limit L, varying along the time axis.

15. The method according to claim 1, wherein in the step (2), the temperature difference is integrated in real time so as to obtain the integral value I that is real-time.

16. The method according to claim 15, wherein before the step (1), the method further comprises a step of performing constant temperature control: setting a target temperature of the heating unit, preheating the heating unit, and performing constant temperature control on the heating unit based on PID.

17. An electronic cigarette, comprising a heating unit, one or more processors, a memory, and one or more programs stored in the memory, wherein said one or more programs are configured to be driven by said one or more processors and configured to execute the method according to claim 1.

18. The electronic cigarette according to claim 17, further comprising a prompt module, and said one or more processors is further configured to control the prompt module to prompt the number of puffs of smoking.

19. The electronic cigarette according to claim 18, wherein the prompt module is configured to prompt the number of puffs of smoking by voice prompt, display screen prompts, or on/off lights indication.

\* \* \* \* \*